United States Patent [19]
Hensley et al.

Patent No.: US 6,198,280 B1
Date of Patent: Mar. 6, 2001

(54) EDDY CURRENT FLEXIBLE FIELD PROBE DEPLOYED THROUGH A LOADING PLATFORM

(75) Inventors: Gary Lee Hensley, Milwaukee, WI (US); David Justin Watson; Larry Stephen Price, both of Richland, WA (US)

(73) Assignee: Siemens Westinghouse Power Corporation, Orlando, FL (US)

(*) Notice: Subject to any disclaimer, the term of this patent is extended or adjusted under 35 U.S.C. 154(b) by 0 days.

(21) Appl. No.: 09/067,435

(22) Filed: Apr. 27, 1998

(51) Int. Cl.[7] .................. G01R 33/12; G01N 27/82; G01N 27/72
(52) U.S. Cl. .................. 324/237; 324/262; 324/238; 324/225
(58) Field of Search ................... 324/234, 236, 324/237, 238, 239, 240, 241, 242, 243, 262, 225

(56) References Cited

U.S. PATENT DOCUMENTS 4,937,524 * 6/1990 Fasnacht et al. ............... 324/262
5,801,532 * 9/1998 Patton et al. ................... 324/238

* cited by examiner

Primary Examiner—Walter E. Snow
(74) Attorney, Agent, or Firm—Eckert Seamans Cherin & Mellott, LLC

(57) ABSTRACT

Flexible eddy current probes that allow an inspector to interrogate the blade roots or disk slots of different types of blades and disks while using a limited number of probes. The probe includes a rectangular-shaped block assembly, a rectangular-shaped loading platform having a slot therein, and stabilizing slide rods that couple the loading platform to the block assembly. The slide rods are adapted to slide through the block assembly as the block assembly is urged towards the loading platform. The probe further includes a flexible coil within a flexible membrane that produces a magnetic field during the inspection. The flexible coil extends from the block assembly and remains within the device, that is, between the loading platform and the block assembly, when not deployed. When deployed, the flexible coil passes through the slot in the loading platform to allow contact with the surface being inspected. Outriggers within the probe guide the flexible coil onto the surface during deployment.

24 Claims, 2 Drawing Sheets though, and although this technique is very sensitive and effective, it requires multiple probes, fixtures, extensive personnel training and exceedingly costly inspection devices. Using such inspection equipment and techniques, inspection time still is exceedingly large and it is known to take as long as twelve hours to inspect a turbine disk. Such lengthy inspections result in increased downtime and increased costs.

EDDY CURRENT FLEXIBLE FIELD PROBE DEPLOYED THROUGH A LOADING PLATFORM

BACKGROUND OF THE INVENTION

The present invention relates to an improved eddy current probe and a method for using the same and, more particularly, to a flexible eddy current probe that may be utilized to inspect blade roots or disk slots of different types of blades and disks having different surface characteristics.

An eddy current (EC) is an electrical current induced in a conductor by reaction with a magnetic field. Eddy Currents are circular in nature with paths oriented perpendicular to the direction of the applied magnetic field. Eddy current probes, as well as ultrasonic probes, have been utilized to non-destructively inspect surfaces of gas turbines, aircraft engines, and so on, and have especially been utilized to inspect the rotating disks and blade roots thereof.

In general, varying magnetic fields during EC testing are generated by an alternating current flowing through a coil positioned immediately adjacent to the conductor. The magnetic field can vary in magnitude and distribution in relation to the following attributes of the specimen or part being inspected: (1) electrical conductivity; (2) magnetic permeability; (3) geometry; and (4) homogeneity. To yield useful and accurate information from an EC inspection, one must isolate and examine those areas or portions of the specimen on the part undergoing inspection. In order to generate the eddy current, the conductor must remain at the same distance and angle from the surface of the specimen. This distance must be maintained for every subsequent specimen due to component geometry dimensions. The eddy current will decrease as the distance from the coil or surface of the part increases. In practice, eddy current strength drops off so rapidly that the currents are negligible and become undetectable by conventional instrumentation a relatively short distance from the coil. In all instances, the physical size of the conductor housing must allow the probe or coil to be placed consistently in the same position relative to the area being inspected. This effect or response due to geometry changes and coil-to-part spacing is called lift-off In addition to the particular geometry of the part being inspected in relation to the physical characteristics of the EC probe, changes in lift-off also result from surface roughness, slight contour, probe wobble, probe bounce and inconsistencies in the thickness of nonmetallic coating, such as paint, primer, and anodic coating. Due to impedance changes caused by lift-off variations, defects, for example, large cracks or other flaws, in the surface under inspection may not be readily detected by the EC inspection.

In order to overcome the above-mentioned problem, it is necessary to maintain the EC probe at the same angle and distance to the part as the probe passes across its surface. This, however, is virtually impossible to accomplish with a single hand-held EC probe and, thus, the industry has developed and fabricated geometry-specific conductor housings designed to conform to the specific shapes of the parts being inspected. Generally, an EC coil within a particular EC probe is positioned within a block of non-conductive material that is permanently shaped to fit a unique geometry. By utilizing numerous geometry-specific probes to carry out inspections of complex machine or structures, such as highly stressed aircraft frames, turbine blades and disk components, structural flaws and defects are detected with a high degree of accuracy.

Over the past ten years a vast amount of work has been done to expand the coverage of EC probes in order to reduce inspection time. For example, the aircraft industry has developed fixtures that allow the placement of several EC coils within a single fixture design (multi-coil arrays), in accordance with standard practice, to match a part's specific geometry. This example is depicted in a turbine disk. Due to the nature of these highly stressed parts, it is important that each disk slot be inspected along the pressure faces of both sides. Through the use of computer controls, the inspection technician can be assured that all surfaces are scanned with a very high degree of reliability. However, and although this technique is very sensitive and effective, it requires multiple probes, fixtures, extensive personnel training and exceedingly costly inspection devices. Using such inspection equipment and techniques, inspection time still is exceedingly large and it is known to take as long as twelve hours to inspect a turbine disk. Such lengthy inspections result in increased downtime and increased costs.

Thus, current EC probe inspections suffer from the following: (1) a unique probe is required for each different part undergoing inspection; (2) probe failure requires multiple probes for each part; (3) multiple calibration standards are required; (4) a separate probe calibration is required for each type of part inspected; (5) extensive development efforts and time are required to make new probes; and (6) substantial expense is incurred since EC probes are expensive.

It is therefore an object of this invention to provide an improved eddy current probe that overcomes the above-mentioned disadvantages of prior EC probes.

It is another object of this invention to provide an eddy current probe that can be used to interrogate parts with different surface structures and geometries.

It is a further object of this invention to provide an eddy current probe that reduces inspection time.

It is still another object of this invention to provide an eddy current probe that allows for the inspection of the entire surface of the part under inspection in only a single pass of the probe.

Various other objects, advantages and features of the present invention will become readily apparent to those of ordinary skill in the art, and the novel features will be particularly pointed out in the appended claims.

SUMMARY OF THE INVENTION

In accordance with an embodiment of the present invention, an eddy current inspection probe includes a rectangular-shaped block assembly, a rectangular-shaped loading platform having a slot therein, and stabilizing slide rods that couple the loading platform to the block assembly. The slide rods are adapted to slide through the block assembly as the block assembly is urged towards the loading platform. The probe further includes a flexible coil that produces a magnetic field during the inspection. The flexible coil is coupled to and extends from the block assembly and remains between the loading platform and the block assembly when not deployed. To deploy the flexible cable, the block assembly is urged towards the loading platform whereupon the flexible coil passes through the slot in the loading platform and comes into contact with the surface to be inspected.

As an aspect of the present invention, the slide rods are biased away from the block assembly so that the flexible coil is prevented from being deployed when the loading platform is not urged towards the block assembly.

As another aspect of the present invention, the probe includes outrigger rods that extend from the block assembly and guide the flexible coil onto a surface to be inspected during coil deployment.

As a further aspect of the present invention, the flexible coil is retained with a flexible member that functions to change shape as the flexible coil is guided onto the surface to be inspected.

As an additional aspect of the present invention, the loading platform includes an upper U-shaped portion for retaining the flexible coil when not deployed and a lower portion having a surface that is adapted to contact the surface to be inspected.

As a feature of this aspect, the surface of the lower portion is substantially sloped.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF CERTAIN PREFERRED EMBODIMENTS

The improved eddy current probe of the present invention is identified herein as the eddy current flexible field probe or simply the flexible field probe (FFP). As will be clear from the description below, the FFP of the present invention allows a technician to inspect a blade root or disk slot with a minimum of lift-off by utilizing only the FFP. The net result is a quicker, more accurate and lower-costing inspection. Laboratory and subsequent field trials have shown that the innovative design of the present invention eliminates much of the probe wobble/lift-off problems encountered with traditional probe designs. Further testing and application has further shown that one FFP will fit and inspect multiple brands of gas turbines including, for example, the Siemens stage one V84.2, the GE Frame 7 and the Westinghouse 501 series gas turbines.

Figure 1:
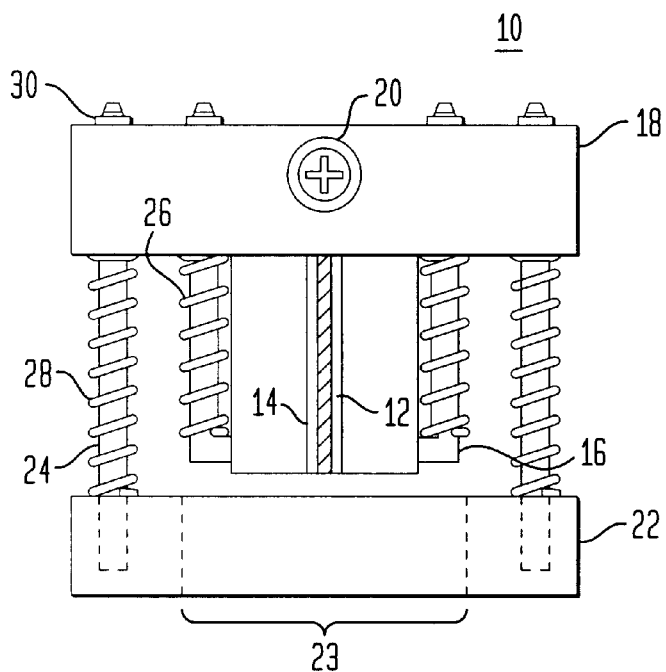
FIG. 1 is a front view of the eddy current flexible field probe of the present invention.
Figure 2:
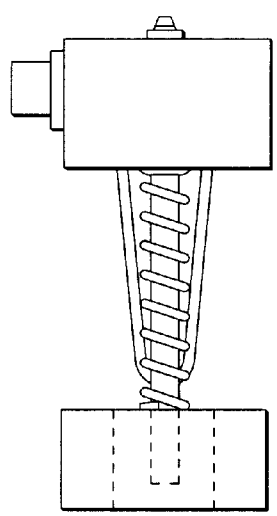
FIG. 2 is a side view of the eddy current flexible field probe of the present invention.

The FFP of the present invention has a driver wired in a differential mode and is wound to operate over a range of 1–6 MHz. Referring now to FIGS. 1 and 2 of the drawings, the flexible field probe 10 is shown as including a flexible coil 12, a flexible membrane 14, two outriggers 16, a coil block assembly 18, an electrical connector 20, a loading platform 22 and two stabilizing slide rods 24. Flexible coil 12 is placed along and within flexible membrane 14 and is housed in a Delrin holding device that is designed to locate and set on top of an inspection surface. The flexible coil along with the flexible membrane form the coil assembly. Flexible membrane 14 operates to change the dimensional aspects of the probe thus minimizing lift-off. Outriggers 16 function to allow the coil assembly to change shape with the varying geometries of the surface being inspected.

Slide rods 24 and outriggers 16 are adapted to slide through coil block assembly 18 during deployment of the probe (discussed below) and rod keepers 30 (more clearly shown in FIG. 5) are coupled to the ends of the outriggers and slide rods to prevent the outriggers and rods from fully passing through the coil block assembly. Each outrigger 16 includes thereon a respective outrigger spring 26 and each slide rod 24 includes thereon a respective stabilizing slide rod spring 28. Loading platform 22 is attached at its two ends to the ends of the stabilizing slide rods 24 and includes therein an internal slot 23 through which the flexible coil passes during deployment. While not deployed, the coil assembly, which includes flexible coil 12 and flexible membrane 14, is retained between loading platform 22 and block assembly 18 in the manner shown in FIG. 1. In addition, internal slot 23 is adapted (i.e., sized) to not allow outriggers 16 to pass therethrough, for example, during deployment of the coil assembly.

During use of the FFP, an appropriate electrical source is supplied to the FFP via electrical connector 20. Prior to inspection, the FFP, like all probes, needs to be calibrated which is accomplished by positioning the probe onto a calibration piece containing an elector discharge notch (EDM) of, for example, .030"×0.15"×.003". Calibration is performed in a manner well known in the art. Upon completion of calibration, the FFP of the present invention is ready to inspect a surface.

In operation, the spring-loaded outrigger 16 is used to position the FFP in the slot of the blade or disk to ensure proper sensor coverage. Loading platform 22 is utilized to align the FFP and to ensure proper outrigger deployment. As previously mentioned, the loading platform has an internal slot 23. The internal slot operates to protect the flexible coil assembly when not deployed and to allow the coil assembly to move up and down in the slot for deployment. The loading platform's stabilizing slide rods 24 properly guide the coil block assembly as the operator loads the FFP.

Figure 3:
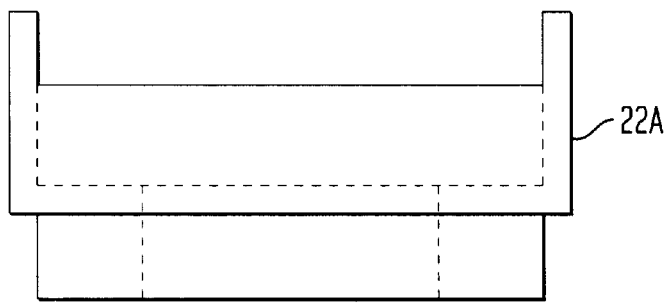
FIG. 3 is a front view of another loading platform that may be used with the eddy current flexible field probe of the present invention.
Figure 4:
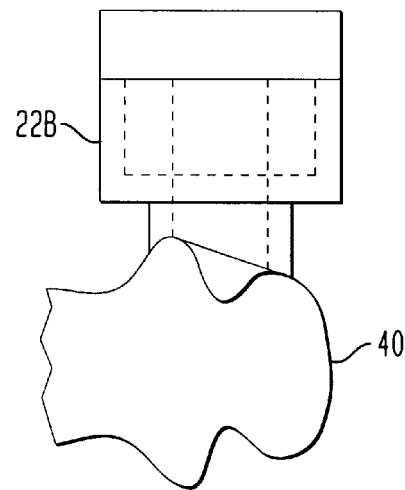
FIG. 4 is an illustration of a loading platform of the eddy current flexible field probe of the present invention in contact with a surface to be inspected.
Figure 5:
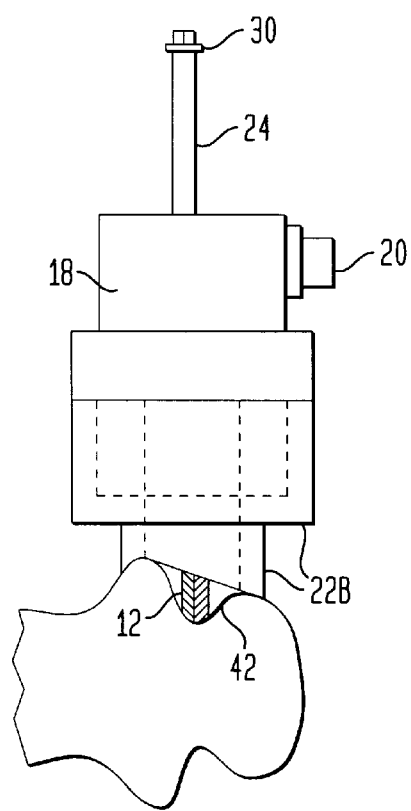
FIG. 5 is an illustration of the eddy current flexible field probe of the present invention with its flexible coil shown in contact with the surface to be inspected.

FIG. 3 is a schematic illustration of another loading platform 22A that may be used in place of loading platform 22 shown in FIGS. 1 and 2. As shown, loading platform 22A essentially includes two halves, a top U-shaped half that retains the coil assembly when not deployed and a bottom rectangular-shaped half that is adapted to contact the surface to be inspected. When deployed, the coil assembly passes from within the top half of loading platform 22A through the internal slot and through the bottom half until it contacts the surface to be inspected. Although the FFP of the present invention having thereon a particular loading platform is capable of inspecting surfaces having an array of physical configurations, all possible configurations cannot be inspected using one type of loading platform. Thus, a loading platform having a different shape, e.g., such as shown in FIG. 3, may be utilized depending on the physical structure of the part being inspected. FIG. 4 partially illustrates a flexible field probe in accordance with the present invention having thereon the preferred type of loading platform 22B. As shown, loading platform 22B, like loading platform 22A, includes top and bottom halves, but the bottom half is sloped so as to conform to the shape of a variety of blades. FIG. 5 schematically illustrates the FFP of the present invention in the deployed position wherein the coil assembly is in contact with a surface 42 of the inspection zone.

When the probe is properly positioned over a part 40 to be inspected (FIGS. 4 and 5), the operator applies downward pressure on block assembly 18 to deploy the flexible coil assembly through slot 23 of the loading platform. During deployment, slide rods 24 are forced upwards extending through block assembly 18 (FIG. 5). Outriggers 16 also are forced upwards extending through block assembly 18 since the outriggers do not pass the loading platform. The flexible coil assembly (flexible coil 12 within flexible membrane 14) extends and fills inspection surface 42 in the manner shown in FIG. 5. The probe is then scanned along the inspection surface while the technician monitors the probe's display (not shown), and within a relatively short scan period (e.g., from one to five seconds) the disk or blade slot is thoroughly inspected. Eddy current inspection is carried out in a manner well known in the art and thus further description thereof is omitted herein. Upon completion of the inspection, the probe is removed at which time the springs expand thereby retracting the coil inside the housing for protection. The probe is then ready to inspect the next slot.

As previously discussed, the flexible field probe of the present invention allows an inspector to interrogate the blade roots or disk slots of several different types of blades and disks while using a limited number of probes. One probe generally will fit various components of different devices produced by different manufactures including, for example, a Siemens stage one blade, a GE stage one blade, an ABB stage one blade, a Westinghouse stage one blade, etc. By using only a single probe, expenses related to the purchase and maintenance of different probes that are designed for unique purposes are substantially reduced.

The flexible field probe of the present invention is compact so that it can be used in the field as well as in the manufacturing facilities. In addition, the following advantages are realized by the flexible field probe of the present invention: (1) one probe will fit numerous parts; (2) the use of one probe reduces expenses and time required to maintain and development unnecessary probes; (3) inspection time is substantially reduced (e.g., by 25%); (4) 100% of the inspection surface can be inspected in only one pass of the probe; (5) there is a reduction in expensive multiple standards and probes; (6) another FFP embodying the present invention may be utilized in the event of a probe failure; and (7) research has indicated that two FFPs will replace the sixteen standard probes that currently are used to inspect, for example, gas turbines.

While the present invention has been particularly shown and described in conjunction with a preferred embodiment thereof, it will be readily appreciated by those of ordinary skill in the art that various changes may be made without departing from the spirit and scope of the invention. For example, although the present invention has been described with reference to the inspection of gas turbines, the present invention may be generally applied to other devices (e.g., aerospace engines) in which surface examination is required.

As another example, although the disclosed embodiment includes two outriggers, two stabilizing slide rods, etc., the flexible field probe of the present invention may include any appropriate number of such devices, for example, four outriggers, four slide rods, etc.

Therefore, it is intended that the appended claims be interpreted as including the embodiments described herein, the alternatives mentioned above, and all equivalents thereto.

What is claimed is:

1. An inspection probe, comprising:
    a block assembly;
    a loading platform extending from said block assembly and including a slot therein;
    loading platform retainment means for movably retaining said loading platform towards and away from said block assembly; and
    a flexible coil operable to produce a magnetic field and coupled to and extending from said block assembly, said flexible coil being positioned between said loading platform and said block assembly when not deployed, and said flexible coil passing through said slot in said loading platform when deployed as said loading platform is moved towards said block assembly.

2. The inspection probe of claim 1, wherein said loading platform retainment means includes biasing means for biasing said loading platform towards a position away from said block assembly.

3. The inspection probe of claim 1, further comprising outrigger means coupled to said block assembly for guiding said flexible coil onto a surface to be inspected as said flexible coil is deployed.

4. The inspection probe of claim 1, further comprising a flexible member coupled to and extending from said block assembly, said flexible coil being retained along and within said flexible member, said flexible membrane functioning to change shape as said flexible coil is guided onto a surface to be inspected.

5. The inspection probe of claim 1, further comprising guiding means coupled to said block assembly for guiding said flexible coil onto a surface to be inspected, said guiding means being operable to minimize lift-off of said flexible coil relative to said surface.

6. The inspection probe of claim 1, wherein said loading platform includes an upper U-shaped portion for retaining said flexible coil when not deployed and a lower portion having a surface adapted to contact a surface to be inspected.

7. The inspection probe of claim 6, wherein the coil assembly when deployed passes from within the top half of said loading platform through the slot and through the bottom half of said loading platform until said coil assembly contacts the surface to be inspected.

8. The inspection probe of claim 6, wherein the surface of the lower portion is substantially sloped.

9. The inspection probe of claim 1, wherein the flexible coil is operable to produce an eddy current in a surface to be inspected.

10. An inspection probe, comprising:
    a rectangular-shaped block assembly, said block assembly having first and second ends;
    a rectangular-shaped loading platform including a slot therein, said loading platform having first and second ends;
    first and second slide rods, a first end of each of said first and second slide rods being coupled to said loading platform, and a second end of each of said first and second slide rods being slidably coupled to said block assembly and being slidable therethrough; and
    a flexible coil operable to produce a magnetic field and coupled to and extending from a center of said block assembly between said first and second ends thereof, said flexible coil being positioned between said loading platform and said block assembly when not deployed, and said flexible coil passing through said slot in said loading platform when deployed as said loading platform and the first end of each of said first and second slide rods are urged towards said block assembly, said second end of each of said first and second slide rods sliding through said block assembly as said first and second slide rods are urged towards said block assembly.

11. The inspection probe of claim 10, further comprising biasing means for biasing the first end of each of said first and second slide rods away from said block assembly so that the flexible coil is prevented from being deployed when the loading platform is not urged towards said block assembly.

12. The inspection probe of claim 10, further comprising first and second outrigger rods extending from and coupled to said block assembly for guiding said flexible coil onto a surface to be inspected as said flexible coil is deployed.

13. The inspection probe of claim 12, wherein said loading platform is adapted to prevent said first and second outrigger rods from passing therethrough as said flexible coil is deployed.

14. The inspection probe of claim 12, wherein said first and second outrigger rods are slidably coupled to said block assembly and are slidable therethrough, and said first and second outrigger rods include outrigger biasing means for biasing said first and second outrigger rods away from said block assembly.

15. The inspection probe of claim 10, further comprising a flexible member, said flexible coil being retained along and within said flexible membrane, said flexible membrane functioning to change shape as said flexible coil is guided onto a surface to be inspected.

16. A method of inspecting a surface, comprising the steps of:
  providing a probe having a block assembly, a loading platform movably extending from the block assembly and a flexible coil extending from the block assembly;
  positioning the loading platform of the probe on the surface to be inspected;
  urging the block assembly of the probe towards the loading platform, the flexible coil being deployed through a slot within the loading platform and extending towards and filling the surface to be inspected as the block assembly moves toward the loading platform; and
  causing the flexible coil to produce a magnetic field.

17. The method of claim 16, wherein the step of urging results in the deployment of the flexible coil from a position between the loading platform and the block assembly through the slot within the loading platform to a position in close proximity to said surface to be inspected.

18. The method of claim 16, wherein the probe includes an outrigger coupled to the block assembly; and the step of urging the block assembly of the probe towards the loading platform includes the step of guiding by the outrigger of the flexible coil onto the surface to be inspected as the flexible coil is deployed.

19. The method of claim 16, further comprising the step of producing an eddy current in the surface to be inspected from the magnetic field produced by the flexible coil.

20. The method of claim 19, further comprising the step of detecting the eddy current produced in the surface to be inspected.

21. A method of inspecting a surface, comprising the steps of:
  providing a probe having a rectangular-shaped block assembly, a rectangular-shaped loading platform including a slot therein, first and second slide rods coupled to the loading platform and slidably coupled to the block assembly, and a flexible coil extending from the block assembly;
  positioning the loading platform of the probe on the surface to be inspected;
  urging the block assembly of the probe towards the loading platform, the slide rods passing through the block assembly as the block assembly moves toward the loading platform, and the flexible coil being deployed through the slot within the loading platform and extending towards and filling the surface to be inspected as the block assembly moves toward the loading platform; and
  causing the flexible coil to produce a magnetic field.

22. The method of claim 21, wherein the probe includes outrigger rods extending from and coupled to the block assembly; and wherein said step of urging the block assembly of the probe towards the loading platform includes the step of guiding by the outrigger rods of the flexible coil onto the surface to be inspected as the flexible coil is deployed.

23. The method of claim 21, further comprising the step of preventing the outrigger rods from passing through the slot as the flexible coil is deployed.

24. The method of claim 21, further comprising the steps of producing an eddy current in the surface to be inspected from the magnetic field produced by the flexible coil and detecting the eddy current produced in the surface to be inspected.

* * * * *